(12) United States Patent
Minamite et al.

(10) Patent No.: US 6,698,665 B2
(45) Date of Patent: Mar. 2, 2004

(54) FRAGRANCE EMITTING APPARATUS

(75) Inventors: Yoshihiro Minamite, Toyonaka (JP); Chie Nakano, Osaka (JP)

(73) Assignee: Dainihon Jochugiku Co., Ltd., Osaka (JP)

( * ) Notice: Subject to any disclaimer, the term of this patent is extended or adjusted under 35 U.S.C. 154(b) by 16 days.

(21) Appl. No.: 10/349,942

(22) Filed: Jan. 24, 2003

(65) Prior Publication Data

US 2003/0146294 A1 Aug. 7, 2003

(30) Foreign Application Priority Data

| Jan. 25, 2002 | (JP) | ........................................ | 2002-016390 |
| Aug. 2, 2002 | (JP) | ........................................ | 2002-226051 |
| Jan. 6, 2003 | (JP) | ........................................ | 2003-000015 |

(51) Int. Cl.⁷ .............................. A61L 9/04; A24F 25/00
(52) U.S. Cl. .............................. 239/44; 239/34; 239/43; 239/45; 239/55; 239/57; 239/60; 239/211
(58) Field of Search ............................ 239/211, 34, 43, 239/44, 45, 54, 55, 57, 60

(56) References Cited

U.S. PATENT DOCUMENTS

| 355,982 | A | * | 1/1887 | Eggert, Jr. .................... 239/44 |
| 1,989,883 | A | * | 2/1935 | Redwine ....................... 239/44 |
| 2,492,039 | A | * | 12/1949 | Gilowitz ....................... 239/44 |
| 2,507,899 | A | * | 5/1950 | Gilowitz ....................... 239/44 |
| 3,400,890 | A | * | 9/1968 | Gould ........................... 239/36 |
| 4,919,981 | A | * | 4/1990 | Levey et al. .................. 239/44 |
| 5,077,102 | A | * | 12/1991 | Chong .......................... 239/44 |
| 5,725,152 | A | * | 3/1998 | Akyu ........................... 239/45 |
| 5,776,561 | A | * | 7/1998 | Lindauer ...................... 239/34 |

FOREIGN PATENT DOCUMENTS

| JP | U 63-158923 | 10/1988 |
| JP | A 5-132807 | 5/1993 |

* cited by examiner

Primary Examiner—Robin O. Evans
(74) Attorney, Agent, or Firm—Oliff & Berridge, PLC

(57) ABSTRACT

The present invention provides a fragrance emitting apparatus comprising: a container body containing an aqueous solution of a perfume composition; a sucking wick held at an opening part of a top of the container body and for sucking the aqueous solution; and a vaporizing part disposed on a top of the sucking wick and for volatizing the aqueous solution sucked through the sucking wick, wherein a part or all of the vaporizing part is covered with an artificial flower that is made of a fabric, a plastic or a combination thereof and that has an apparent volume of 200 to 1500 cm³. The apparatus is excellent in volatizing capability of perfume composition and usability and has also high interior decorating performance.

7 Claims, 2 Drawing Sheets

FRAGRANCE EMITTING APPARATUS

BACKGROUND OF THE INVENTION

1. Field of the Invention

The present invention relates to a fragrance emitting apparatus, and more particularly the fragrance emitting apparatus improved in volatizing capability and usability and having also interior decorating performance.

2. Description of the Prior Art

In recent years, in order to make living space comfortable, fragrance emitting apparatuses of liquid type using fragrance composition solution are widely used. It is generally known that the fragrance emitting apparatuses of this type include a type of sucking wick in which a perfume composition solution sucked through a sucking wick is volatized from a volatizing part and a type of impregnation in which a perfume composition solution previously impregnated or dropped into a volatizing part composed of a ceramic ware or an wooden piece is exhaled.

However, fragrance emitting apparatuses of the sucking wick type are not necessarily sufficient to control a volatizing amount of a perfume composition solution or prevent the solution from leaking out, or are not satisfactory in interior decorating performance although it can visually confirm a decrease of the solution with use. On the other hand, ones of the impregnation type have problems that it is difficult to know a remaining amount of a perfume composition solution and to vaporize perfume continuously as perfume composition to be impregnated is limited.

As attempts for providing the perfume emitting apparatuses of the sucking wick type with an interior decorating performance, for example Japanese Utility Model Laid-open No. 63-158923 or Japanese Patent Laid-open No. 5-132807 discloses a device or an invention in which the apparatus is combined with an artificial flower. However, the apparatuses is merely provided with artificial flowers in a simple manner. Therefore, it is a present state in the perfume emitting apparatuses of the sucking wick type that they are not considered on overall performances including durability of volatizing perfume.

SUMMARY OF THE INVENTION

Taking the present status of the perfume emitting apparatuses as mentioned above into account, it is an object of the present invention to provide a fragrance emitting apparatus improved in volatizing capability and usability and having also interior decorating performance.

In order to attain the above-mentioned object, the present inventors found that an aimed perfume emitting apparatus is obtained by combining a specific vaporizing part with an artificial flower when a perfume composition contained in a container body is exhaled through a sucking wick, and have completed the present invention.

That is, the present invention relates to a fragrance emitting apparatus comprising: a container body containing an aqueous solution of a perfume composition; a sucking wick held at an opening part of a top of the container body and for sucking the aqueous solution; and a vaporizing part disposed on a top of the sucking wick and for volatizing the aqueous solution sucked through the sucking wick, wherein a part or all of the vaporizing part is covered with an artificial flower that is made of a fabric, a plastic or a combination thereof and that has an apparent volume of 200 to 1500 $cm^3$.

In addition, preferred embodiments among the fragrance emitting apparatuses of the present invention include for example the followings:

the fragrance emitting apparatus, wherein the vaporizing part is a felt or sheet made of a plastic fiber or a natural fiber, and has a surface area of 10 to 80 $cm^2$;

the fragrance emitting apparatus, wherein the vaporizing part is provided with a support for holding it, and the support is provided detachably with a supporting stand for holding the artificial flower;

the fragrance emitting apparatus, wherein the supporting stand has a plurality of holes on a base face thereof, and a ratio of total area of the holes to a surface area of the base face ranges from 0.3 to 0.7, thereby a amount that the aqueous solution is vaporized into an air is set to 1 to 8 ml a day;

the fragrance emitting apparatus, wherein the support is fitted and fixed with a locking part formed along a periphery of the container body;

the fragrance emitting apparatus, wherein the container body is placed in a wrapping body; and the fragrance emitting apparatus, wherein be wrapping body is in a shape of a basket or pot, or a wrapping material.

DETAILED DESCRIPTION OF THE PREFERRED EMBODIMENTS

The container body used in the fragrance emitting apparatus of the present invention is not specifically limited in its material or structure, and may be made of plastic, ceramic ware, glass or the like, and is preferably a transparent or semi-transparent plastic container an amount of the aqueous solution in which can be visually confirmed. Generally, it is practical when the volume of the container body ranges from 50 ml to 300 ml. In addition, it is preferable to form a slight recess in a part of the base of the container body on which the sucking wick abuts so that the aqueous solution of the perfume composition could be entirely sucked up.

Holding of the sucking wick in the opening part of the top of the container body may be carried out with, for example, an inside plug fitted in the opening part. The inside plug is preferably made of a plastic. In addition, the inside plug can surely hold the sucking wick and is suitable when it is formed in a shape of tube downwardly from a part at which it is fitted in the container body so that the sucking wick could be inserted therein.

The sucking wick used in the present invention needs to be stable to the aqueous solution of the perfume composition and suck the aqueous solution through capillary action, and the concrete material thereof includes, for example plastic fibers, such as nylon, polyester or the like, natural fibers, or woods. Among them, it is easy to use felt sucking wicks composed of a plastic fiber or natural fiber. Further, the sucking wick can be formed in a stick or twine shape having a outer diameter of about 3 to 10 mm according to the places and purposes in or for which the fragrance emitting apparatus is used.

Also, the perfume composition is not specifically limited, and can be selected from natural perfumes and synthetic perfumes. For example, the natural perfumes include orange oil, lemon oil, lime oil, citron oil, lavender oil, peppermint oil, eucalyptus oil, jasmine oil, hinoki (Japanese cypress) oil, green tea essential oil and the like, and the synthetic perfumes include linalool, citronelool, geraniol, phenylethyl alcohol, amyl cinnamic aldehyde, cumin aldehyde, benzyl acetate, limonene, α-pinene, δ-dodecalactone and the like. The perfumes may be used alone or in a mixed state in which two or more perfumes are mixed. To the perfume(s) and water, an aqueous organic solvent represented by alcohol, glycol or glycol ether, etc. a surfactant, a solubilization agent, a stabilizing agent, a colorant and the like are suitably mixed to give an aqueous solution of a perfume composition.

In the fragrance emitting apparatus of the present invention, the vaporizing part from which an aqueous solution of a perfume composition sucked through a sucking wick is volatized is disposed on the top of the sucking wick. The vaporizing part is in a shape of felt or sheet, and the material thereof includes, for example plastic fibers, such as nylon, polyester or the like, natural fibers, or woods similarly to the sucking wick. Among them, the vaporizing part in a shape of felt or sheet composed of a plastic fiber or natural fiber fits the object of the present invention and is preferable. It is preferable that the vaporizing part is formed in a roughly circular shape having a thickness of 2 to 15 mm and a surface area of 10 to 80 $cm^2$. By disposing the vaporizing part on the top of the sucking wick so that the base of the vaporizing part can abut the top face of the sucking wick, the solution sucked through the sucking wick is passed into the vaporizing part, and therefrom the solution is gradually exhaled into an air. In the meantime, when the surface area of the vaporizing part is less than 10 $cm^2$, the volatizing amount of the solution tends to decrease, while when the surface area thereof is more than 80 $cm^2$, it often occurs some problems in durability of perfume emitting.

It is preferable to dispose a support for holding the vaporizing part and to dispose detachably a supporting stand for holding the artificial flower on the support. As the supporting stand, for example a plastic sheet having a thickness of about 1 to 3 mm can be used, and the plastic sheet may have a plurality of holes on the base face thereof. In this case, when the ratio of total area of the holes to the surface area of the base face (hereinafter, referred to also as "hole ratio") ranges from 0.3 to 0.7, the volatizing amount of the perfume can be controlled. In addition, when the support is fitted and fixed with a locking part formed along a periphery of the container body, an abutment between the vaporizing part and the sucking wick makes easy, and therefore the locking part is a convenient means.

The present invention is characterized in that a part or all of the vaporizing part is covered with an artificial flower that is made of a fabric, a plastic or a combination thereof and that has an apparent volume of 200 to 1500 $cm^3$, and this provides an interior decorating performance and enables the volatizing amount of the perfume to be controlled. The flower kind and color of the artificial flower may be arbitrarily selected. In the meantime, the apparent volume can be suitably selected by considering the volume of the container body, the size of the vaporizing part and the like, and is preferably 250 to 1000 $cm^3$, and more preferably 300 to 500 $cm^3$.

The apparent volume of the artificial flower in the present invention means a value determined according to the following measurement procedure:

(i) First of all, the artificial flower part of the artificial flower is placed in a plastic bag;

(ii) Next, while air in the bag is removed by slightly pressing the bag from the outside thereof, the bag is heat-sealed on the part corresponding to the periphery of the artificial flower; and (iii) Finally, the bag in which the artificial flower is sealed obtained in the process (ii) is sunk into a tell-skirted dish in which water is placed and which has a size more than that of the bag, an increased volume in the dish is measured and the increased volume is determined as "the apparent volume of the artificial flower".

For example, a fragrance emitting apparatus comprising a felt or sheet vaporizing part that has a surface area of 10 to 80 $cm^2$ and is made of a plastic fiber or a natural fiber, a supporting stand having a hole ratio of 0.3 to 0.7 and an artificial flower having the above-mentioned apparent volume enables the volatizing amount of the aqueous solution of the perfume composition into an air to range from 1 to 8 ml a day, and thereby it is easy to keep fragrance emitting time of 1 to 2 months in case where a container body having a usual volume is used.

Further, in the present invention, from a view point of a further improvement of interior decorating performance and a protection of a container body, the container body may be in a combination with a wrapping body, for example a basket, a pot or wrapping material, etc. For example, the container body may be placed in a basket made of cane (rattan), bamboo, plastic or the like, or a pot made of ceramic ware, earthenware, metal or the like, or may be wrapped with a wrapping material, such as paper, non-woven fabric, fabric or the like. The size and shape of the wrapping body including a basket, a pot and a wrapping material is not limited at all. For example, the wrapping body may have a window through which a decrease of an aqueous solution of a perfume composition can be visually confirmed. In addition, a container body wrapped with a wrapping material may be further placed in a basket or a pot.

The fragrance emitting apparatus of the present invention is excellent in volatizing capability of perfume composition and usability and has also high interior decorating performance. The apparatus gives out not only fragrance but also a beauty view by an ornamental artificial flower over a long-time, for example 1 to 2 months.

EXAMPLES

Next, the fragrance emitting apparatus of the present invention will be described in further detail based on the following examples and test examples to which the present invention is not limited.

Example 1

Figure 1:
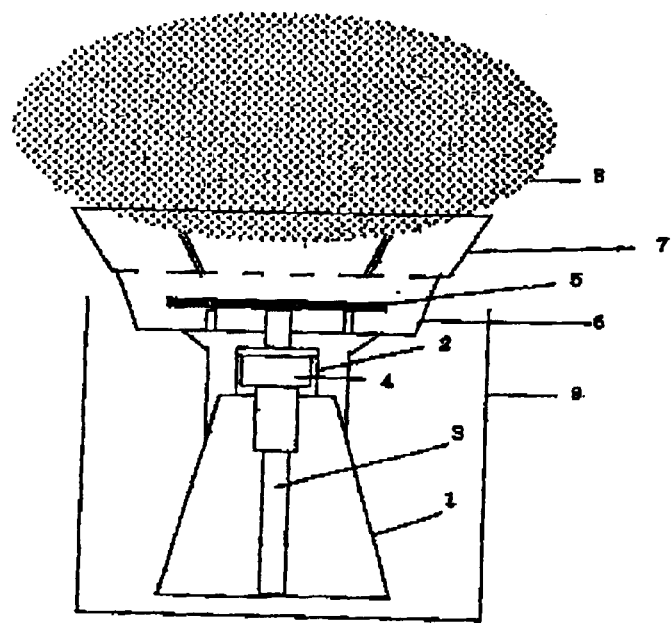
FIG. 1 is a sectional view showing a first embodiment of the fragrance emitting apparatus of the present invention.

FIG. 1 shows a first embodiment of the fragrance emitting apparatus of the present invention.

A container body 1 made of transparent polyester is filled with 120 g of an aqueous solution of a perfume composition comprising 1 g of green tea essential oil, 0.5 g of a nonionic surfactant and 118.5 g of water. An inside plug 4 is fitted in an opening part 2 of the top of the container body 1. A sucking wick 3 composed of stick-like felt having an outer diameter of 7 mm is inserted in the inside plug 4. Then, a support 6 in which a vaporizing part 5 composed of a disk-like felt having a thickness of 5 mm and a diameter of 4.2 cm is placed is fitted and fixed at a periphery of the opening 2 in such a manner that the vaporizing part 5 can abut the top face of the sucking wick 3. A supporting stand 7 on which an artificial flower 8 made of plastic is fixed is detachably provided on the support 6 for the vaporizing part 5. The artificial flower 8 has an apparent volume of 400 cm$^3$, and simulates a hydrangea. The container body 1 is placed in a flower basket 9 from cane to give a fragrance emitting apparatus of the present invention.

The fragrance emitting apparatus was left and used on a sideboard in a living room. It continued to give out fragrance over about 2 months and the artificial flower simulating a hydrangea was an appropriate interior.

Example 2

Figure 2:
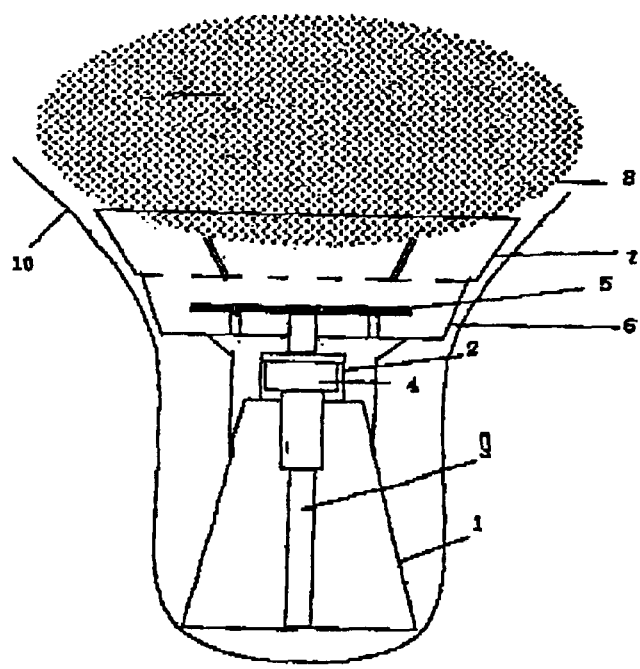
FIG. 2 is a sectional view showing a second embodiment of the fragrance emitting apparatus of the present invention.

FIG. 2 shows a second embodiment of the fragrance emitting apparatus of the present invention in which the container body 1 is wrapped with a wrapping paper 10 instead of being placed in a flower basket.

Example 3

Figure 3:
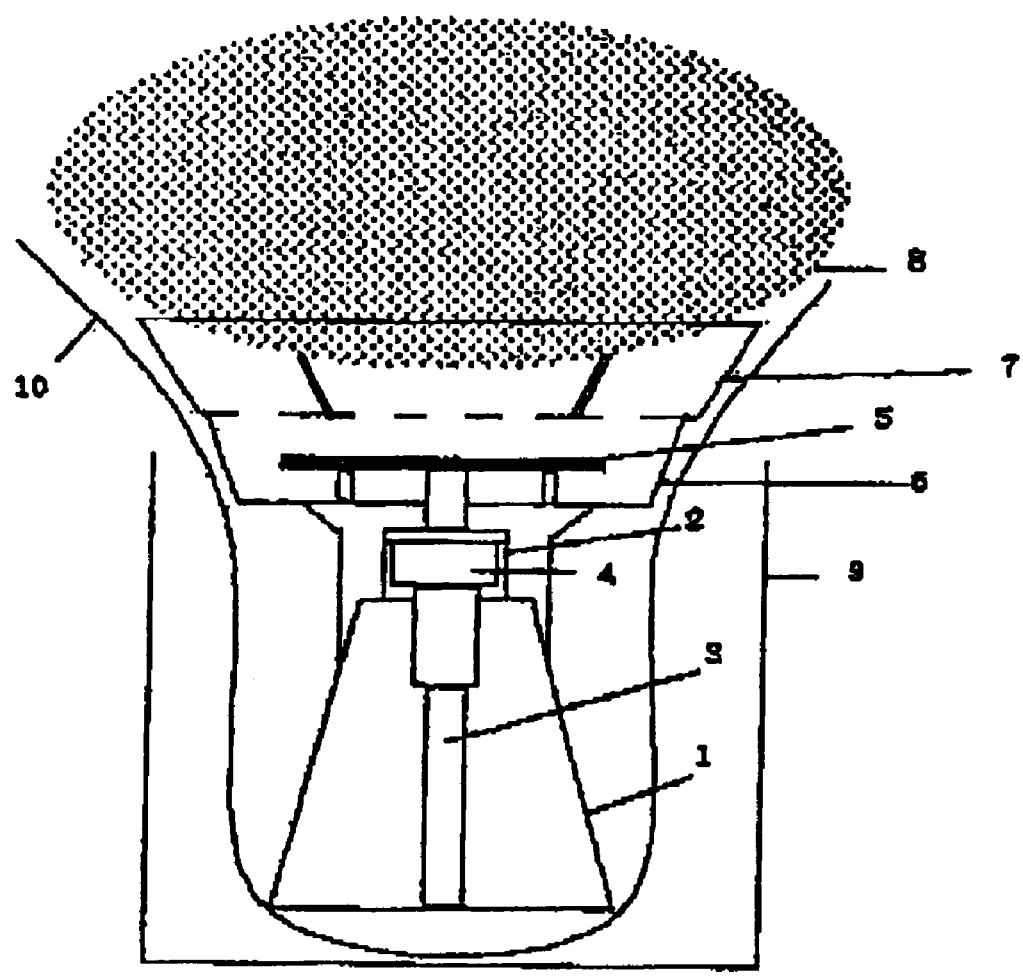
FIG. 3 is a sectional view showing a third embodiment of the fragrance emitting apparatus of the present invention.

FIG. 3 shows a third embodiment of the fragrance emitting apparatus of the present invention in which the container body 1 is first wrapped with a wrapping paper 10 and then placed in a flower basket 9.

Test Example

According to the procedure of Examples 1–3, several fragrance emitting apparatuses shown in Table 1 were prepared, left in a room of 6-tatami mat (9.9 m$^2$) at a temperature of 20° to 25° C. and the following capabilities in them were tested. In the meantime, the aqueous solutions of perfume composition in which green tea essential oil used in Examples 1–3 was substituted with other perfume were used, and sucking wick in stick shape having a diameter of 7 mm was used, and vaporizing parts and artificial flowers indicated in Table 1 were used, respectively.

The capabilities to be tested were (1) durability of fragrance and (2) interior decorating performance. And, general judgement was carried out on the basis of the results of the tested two capabilities.

In the meantime, the durability of fragrance was determined according to the following process: a fragrance emitting apparatus to be tested was placed in a box having a volume of 1.8 m$^3$ every 1 week after starting the test, and the fragrance in the box was assessed by the sense of smell after 10 minutes. The level of fragrance shortly after a fragrance emitting apparatus was started to use was identified as category 5 (standard), and the number of days passed until the level of fragrance was lowed to category 3 based on the following criterion was determined:

Category 5: Level of fragrance is similar to that of a standard;
Category 4: Level of fragrance is slightly inferior to that of a standard;
Category 3: Level of fragrance is relatively inferior to that of a standard;
Category 2: Level of fragrance is considerably inferior to that of a standard;
Category 1: Level of fragrance is largely lowered by comparing with that of a standard and quality of fragrance is deteriorated.

TABLE 1

Structure of Fragrance Emitting Apparatus

| | Perfume Component | Sucking Wick | Vaporizing Part (surface area; cm$^2$) | Artificial flower[1] | Supporting stand[2] | Wrapping Body | Capabilities[3] | | |
|---|---|---|---|---|---|---|---|---|---|
| | | | | | | | A | B | C |
| Present Invention 1 | Green tea oil | Pulp felt | Pulp felt (40) | 300 | 0.8 | Present | 3-w | High | Δ |
| Present Invention 2 | Green tea oil | Pulp felt | Pulp felt (70) | 1500 | 0.5 | Present | 2-m | High | ○ |
| Present Invention 3 | Green tea oli | Pulp felt | Pulp felt (10) | 1000 | 0.7 | Present | 2-m | High | ○ |
| Present Invention 4 | Lime oil | Pulp felt | Pulp felt (30) | 250 | 0.6 | Present | 1-m | High | ○ |
| Present Invention 5 | Limonene | Nylon wick | Nylon fiber (20) | 400 | 0.6 | Present | 2-m | High | ○ |
| Present Invention 6 | Hinoki oil | Nylon wick | Nylon fiber (30) | 600 | 0.5 | Present | 2-m | High | ○ |
| Present Invention 7 | Lavender | Wood | Wood (80) | 450 | 0.3 | Present | 1-m | High | ○ |
| Present Invention 8 | α-Pinene | Wood | Wool felt (80) | 200 | 0.25 | Present | 3-w | High | Δ |
| Comparative Example 1 | Green tea oil | Pulp felt | — | 300 | — | Present | n.d. | High | X |
| Comparative Example 2 | Green tea oil | Pulp felt | Wool felt (120) | 80 | 0.6 | Present | <3-w | Medium | X |
| Comparative Example 3 | Green tea oil | Pulp felt | Pulp felt (70) | — | 0.7 | No | <3-w | Low | X |
| Comparative Example 4 | Green tea oil | Pulp felt | — | — | 0.1 | No | n.d. | Low | X |
| Comparative Example 5 | Commercially available apparatus (type of impregnation) | | | | | | 1-m | Low | X |

[1]The apparent volume of the artificial flower is indicated in the unit of cm$^3$.
[2]The hole ratio of the supporting stand for artificial flower is indicated.
[3]"A", "B" and "C" In the capabilities mean durability of fragrance, interior decorating performance and general judgement, respectively. In the item "A", "w" means week and "m" means month.
n.d.: "n.d." means that the apparatus dose not give out fragrance and therefore can not be judged.

From the results of the test, it is clear that the fragrance emitting apparatus of the present invention is excellent in both of (1) durability of fragrance and (2) interior decorating performance, and that the apparatus has a great practical value. Further it is also clear that the surface area of the vaporizing part ranging from 10 to 80 cm² is particularly preferable, and that the apparent volume of the artificial flower ranging from 200 to 1500 cm³ is appropriate. In addition, the fitting of the supporting stand for the artificial flower on the support for the vaporizing part makes easy to control the volatizing amount of perfume, and therefore it is confirmed that the fitting is a preferable means.

On the other hand, fragrance emitting apparatuses having no vaporizing part (Comparative Examples 1 and 4) have little volatizing amount of perfume, and do not give out a fragrance. Further, a fragrance emitting apparatus (Comparative Example 2) that has an artificial flower covering a vaporizing part and having an apparatus volume of less than 200 cm³ and a fragrance emitting apparatus (Comparative Example 3) having no an artificial flower are insufficient to control the volatizing amount of perfume in addition to no interior decorating performance. Therefore, they do not meet the object of the present invention. In addition, a commercially available apparatus in which a perfume composition is impregnated into a ceramic ware has low interior decorating performance.

What is claimed is:

1. A fragrance emitting apparatus comprising:
    a container body containing an aqueous solution of a perfume composition;
    a sucking wick held at an opening part of a top of the container body and for sucking the aqueous solution; and
    a vaporizing part disposed on a top of the sucking wick an for volatizing the aqueous solution sucked through the sucking wick,
    wherein a part or all of the vaporizing part is covered with an artificial flower that is made of a fabric, a plastic or a combination thereof and that has an apparent volume of 200 to 1500 cm³,
    the vaporizing part is provided with a support for holding it, and the support is provided detachably with a supporting stand for holding the artificial flower, and
    the supporting stand has a plurality of holes on a base face thereof, and a ratio of total area of the holes to a surface area of the base face ranges from 0.3 to 0.7, thereby an amount that the aqueous solution is vaporized into an air ranges from 1 to 8 ml a day.

2. The fragrance emitting apparatus according to claim 1, wherein the vaporizing part is a felt or sheet made of a plastic fiber or a natural fiber, and has a surface area of 10 to 80 cm².

3. The fragrance emitting apparatus according to claim 1, wherein the support is fitted and fixed with a locking part formed along a periphery of the container body.

4. The fragrance emitting apparatus according to claim 3, wherein the container body is placed in a wrapping body.

5. The fragrance emitting apparatus according to claim 2, wherein the container body is placed in a wrapping body.

6. The fragrance emitting apparatus according to claim 1, wherein the container body is placed in a wrapping body.

7. The fragrance emitting apparatus according to claim 6, wherein the wrapping body is in a shape of a basket or pot, or a wrapping material.

* * * * *